US010092647B2

(12) United States Patent
Feugier et al.

(10) Patent No.: US 10,092,647 B2
(45) Date of Patent: Oct. 9, 2018

(54) CANINE HEALTH PRODUCT CONTAINING ANTIBODIES AGAINST CANINE PARVOVIRUS TYPE 2

(71) Applicant: Mars, Incorporated, McLean, VA (US)

(72) Inventors: Alexandre Feugier, Aimargues (FR); Sylvie Chastant, Aimargues (FR); Hanna Mila, Aimargues (FR); Aurelien Grellet, Aimargues (FR)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 14/904,909

(22) PCT Filed: Jul. 9, 2014

(86) PCT No.: PCT/EP2014/064711
§ 371 (c)(1),
(2) Date: Jan. 13, 2016

(87) PCT Pub. No.: WO2015/004181
PCT Pub. Date: Jan. 15, 2015

(65) Prior Publication Data
US 2016/0213778 A1 Jul. 28, 2016

(30) Foreign Application Priority Data

Jul. 9, 2013 (EP) ..................................... 13305976
Mar. 13, 2014 (GB) ................................... 1404503.3

(51) Int. Cl.
*A61K 39/42* (2006.01)
*A61K 39/40* (2006.01)
*A61K 45/06* (2006.01)
*C07K 16/06* (2006.01)
*C07K 16/08* (2006.01)
*C07K 16/10* (2006.01)
*C07K 16/12* (2006.01)
*A61K 39/00* (2006.01)

(52) U.S. Cl.
CPC .............. *A61K 39/42* (2013.01); *A61K 39/40* (2013.01); *A61K 45/06* (2013.01); *C07K 16/06* (2013.01); *C07K 16/081* (2013.01); *C07K 16/087* (2013.01); *C07K 16/1027* (2013.01); *C07K 16/1225* (2013.01); *A61K 2039/505* (2013.01); *A61K 2039/507* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| 4,652,448 | A | * | 3/1987 | Sadowski | .......... | C07K 16/1232 |
| | | | | | | 424/150.1 |
| 7,682,619 | B2 | * | 3/2010 | Dubovi | ................ | A61K 39/145 |
| | | | | | | 424/184.1 |
| 7,794,720 | B2 | | 9/2010 | Wilson | | |
| 8,052,971 | B2 | | 11/2011 | Meyer | | |
| 2007/0154484 | A1 | * | 7/2007 | Meyer | .................. | C07K 16/081 |
| | | | | | | 424/169.1 |
| 2007/0264264 | A1 | * | 11/2007 | Evans | ..................... | C07K 16/10 |
| | | | | | | 424/157.1 |
| 2011/0020461 | A1 | * | 1/2011 | Leneau | ................. | A61K 31/728 |
| | | | | | | 424/535 |
| 2016/0213778 | A1 | * | 7/2016 | Feugier | .................. | C07K 16/06 |

FOREIGN PATENT DOCUMENTS

| WO | 2004105792 | 12/2004 |
| WO | WO 2005/077299 | * 8/2005 |

OTHER PUBLICATIONS

Schultz et al. (Journal of Comparative Pathology. 2010; 142: S102-S108).*
Ikemori et al. (Veterinary Microbiology. 1997; 58: 105-111).*
Fu et al. (Journal of Virological Methods. 2006; 133: 112-115).*
Gillette et al. (American Journal of Physiology—Legacy Content. 1966; 210 (2): 419-422).*
Carmichael et al. (Proceedings of the Society for Experimental Biology and Medicine. 1962; 109 (3): 677-681).*
Bioindist, Co., Ltd., "Caniwell—Milk a special Milk Food for Pet Animals", Product Brochure.
Nguyen, et al., "Passive Protection of dogs against Clinical Disease due to Canine Parvovirus-2 by Specific Antibody from Chicken Egg Yolk", The Canadian Journal of Veterinary Research, 2006, 70: 62-64.
Root Kustritz, "Small Animal Pediatrics and Theriogenology", Jan. 1, 2010, XP55143079.
Merial, "Treatment of Infectious Diseases Caused by ParvoVirus Type 2 in Dogs in a Nursery", Veterinary Doctor, Jan. 2007, p. 32.
Day, et al., Guidelines for the Vaccination of Dogs and Cats Compiled by the Vaccination of Guidelines Group (VGG) of the World Small Animal Veterinary Association (WSAVA), Journal of Small Animal Practice, vol. 51, Jun. 2010, pp. 338-356.
Parker, "Treating neonatal and pediatric hypoglycemia", Banfield, Jan. 1, 2006, pp. 34-42.

* cited by examiner

*Primary Examiner* — Shanon A. Foley
(74) *Attorney, Agent, or Firm* — Mars, Incorporated

(57) ABSTRACT

The present invention relates to a composition which includes antibodies against one or more specified virus, bacteria and/or pathogen for use to improve dog health, wherein the composition is administered before 24 hours of age of the dog or between 24 hours and up to 90 days of age of the dog.

8 Claims, 2 Drawing Sheets

CANINE HEALTH PRODUCT CONTAINING ANTIBODIES AGAINST CANINE PARVOVIRUS TYPE 2

Figure 1:
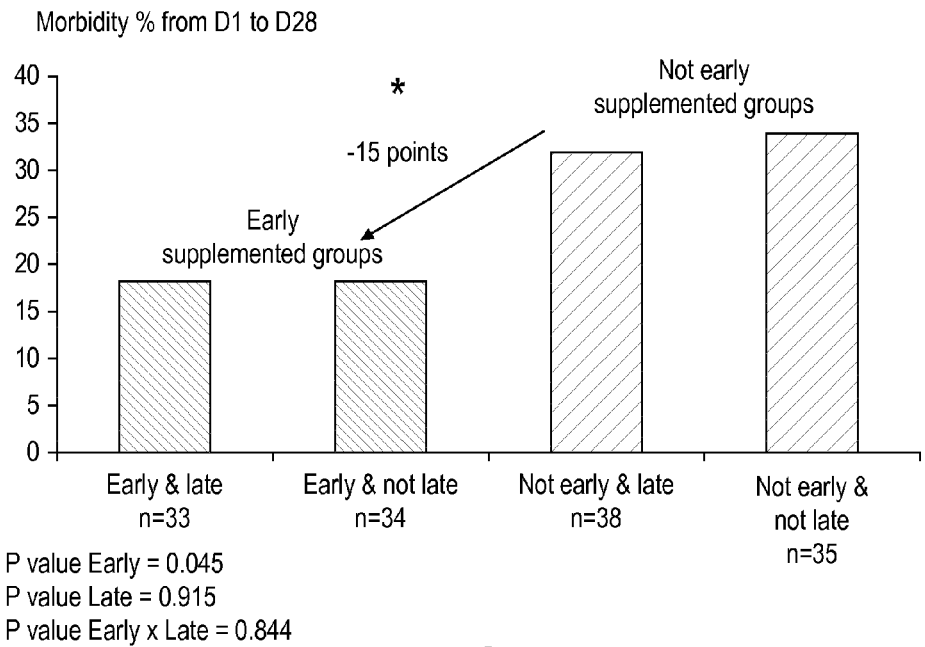

The present invention relates to a composition which includes antibodies against one or more specified virus, bacteria and/or pathogen for use to improve dog health, wherein the composition is administered before 24 hours of age of the dog or between 24 hours and up to 90 days of age of the dog.

The mortality rate of puppies in dog breeding from birth to weaning (2 months of age) is dramatically high and evaluated around 25%. Infectious diseases, in particular septicemia and diarrhea are the major cause of puppy death. This also has negative impacts on dog growth performances.

The present invention addresses this problem.

A first aspect of the invention provides a composition containing antibodies against one or more of the following;
Virus:
  Canine parvovirus type 2,
  Canine Herpesvirus,
  Canine parainfluenza virus
  Canine distemper virus
  Canine coronavirus
  Adenovirus type 1
Bacteria:
  Bordetella bronchiseptica
  E. coli
  Streptococci
  Staphylococci
Parasite:
  Isospora
  Giardia for use to improve dog health, administered before 24 hours of age or between 24 hours onwards, and preferably up to 70 days of age or up to 90 days of age.

The present invention provides a hyperimmunised composition, containing homologous or hererologous antibodies, which is/are specifically directed against dog pathogens and administered in a precise time scheme of either early (before 24 hours of age) or late (24 hours of age or later) or both.

The composition for use according to the first aspect of the invention may also comprise a hydrolysed carbohydrate and/or oil (or fat). The hydrolysed carbohydrate can provide a base for the composition. It may also be useful as a hypoglycemic agent for preventing hypoglycaemia in the puppy. Such an agent can assist in avoiding hypoglycaemia (also known as fading puppy syndrome) in any breed, in particular any Toy Breed. The hydrolysed carbohydrate may be one or more of any simple sugar, maltose, dextrose, maltodextrin or fructose. The hydrolysed carbohydrate may be present in the composition in an amount of between 10 and 50% by weight, for example 15 to 50%, 20 to 40%, 25 to 35% or 5 to 35%.

The composition may also include an oil (which may also be referred to as a fat). The oil provides a suitable inert carrier for the antibodies and is appropriate for administration to a puppy according to the invention. The oil may be a useful source of energy for the puppy. Suitable oils include sunflower oil, soya oil, Colza oil, olive oil, palm oil/copra and/or pork fat. Preferably, the oil is a vegetable fat.

The composition may also include any one or more of the following ingredients: egg powder (preferably chicken), other egg product (preferably chicken), vitamins, minerals, water, colostrum or serum. Preferably the composition does not include whey or whey like products. In addition, or alternatively, the composition may include one or more of: Rice, corn, wheat, animal, milk and vegetable proteins, animal and vegetable fat, beat pulp, corn, soya, fish oil, psyllium, lactoserum, fructo-oligo-saccharide, lecithine from soya, amino acids (L-arginine, DL-méthionine, taurine), minerals (Ca, P, Zn, Fe, Mn, Cu, I, Se), vitamins (A, choline, D3, E, niacine, C, calcium pantothenate, B2, B1, B6, biotine, folic acide, B12, K1), antioxidants.

The amount of antibody to be included in the product can range from 10 to 200 mg of hyperimmunised ingredient (egg powder as an example)/g of product The antibodies can be produced according to any known technology and as discussed in Sa Van Nguyen et al., 2006, 70:62-64, The Canadian Journal of Veterinary Research. The quantity of hyperimmunized egg powder can be used to define the amount of antibody in the composition (based on a concentration of 25% of IgY) dosage. A range of from 0.24 to 0.36 g hyperimmunised whole egg powder is a suitable range. Assuming 25% of IgY, this corresponds to 0.06 to 0.09 g IgY/100 g of dog. The IgY produced by this production method is not specific.

Alternatively, the antibodies can be produced by vaccinating an animal against a target disease and obtaining antibodies from serum to form part of the composition of the invention.

An hyperimmunised ingredient here is produced by an animal (preferably a livestock animal) receiving the vaccination program of a dog to produce antibodies against dog pathogens in every tissues of its body (meat, serum) or every biological product (milk, egg).

The hyperimmunised solution containing heterologous antibodies specifically orientated against dog pathogens could be eggs after a dog vaccination program has been applied to chickens or other birds. It could be the milk or colostrum of cows, sheep, goats or other mammalian species after a dog vaccination program has been applied on the related animal (cow, sheep, goat or other livestock mammalian species). It could be serum or meat of animals which have followed the same vaccination program as described above.

It is the vaccination response of the animal producing the hyperimmunised solution that creates the specific antibodies.

The composition for use according to the first aspect of the invention is preferable in a format that enables easy administration to a puppy, including puppies in their first day of life. Thus, preferred forms of the composition include a spray, liquid, mousse or gel. Pet food supplements, including a powder to sprinkle onto a liquid and/or gel an/or food are also included. Further included is typical wet or dry food which may be administered to the animal after weaning. Preferably the product is a liquid or a gel which is in a form to enabling spraying into the mouths of puppies or feeding with ease to a puppy.

The composition, in particular, may include antibodies against one or more of the viruses listed and against E. coli. The composition may comprise antibodies against canine coronavirus and/or adenovirus type 1.

Several different products, due to different geolocalisation of the diseases and different site of action (local or systemic) are included according to the present invention.

The invention includes a product, according to the first aspect, which may include:
Antibodies against each of canine parvovirus type 2, canine herpesvirus, canine parainfluenza virus, canine distemper virus, canine corona virus and adenovirus type 1 in combination. The product may alternatively include any combination of two more thereof, such as antibodies against
Canine parvovirus type 2 and canine herpesvirus
Canine parvovirus type 2 and canine parainfluenza virus
Canine parvovirus type 2 and canine distemper virus
Canine parvovirus type 2 and Adenovirus type 1
Canine herpesvirus and canine parainfluenza virus
Canine herpesvirus and canine distemper virus
Canine herpes virus and canine coronavirus
Canine herpes virus and adenovirus type 1
Canine parainfluenza virus and canine distemper virus
Canine parainfluenza virus and canine coronavirus
Canine parainfluenza virus and adenovirus type 1
Canine distemper virus and canine coronavirus
Canine distemper virus and adenovirus type 1
Canine coronavirus and adenovirus type 1
Canine parvovirus type 2, canine herpesvirus and canine parainfluenza virus
Canine parvovirus type 2, canine herpesvirus and canine distemper virus
Canine parvovirus type 2, canine parainfluenza virus and canine distemper virus
Canine herpesvirus, canine parainfluenza virus and canine distemper virus
Canine parvovirus type 2, canine herpesvirus and canine coronavirus
Canine parvovirus type 2, canine herpesvirus and adenovirus type 1
Canine parvovirus type 2, canine parainfluenza virus and canine coronavirus
Canine parvovirus type 2, canine parainfluenza virus and adenovirus type 1
Canine herpesvirus, canine parainfluenza virus and canine coronavirus
Canine herpesvirus, canine parainfluenza virus and adenovirus type 1
Canine parvovirus type 2, canine distemper virus and canine coronavirus
Canine parvovirus type 2, canine distemper virus and adenovirus type 1
Canine herpesvirus, canine distemper virus and canine coronavirus
Canine herpesvirus, canine distemper virus and adenovirus type 1
Canine parainfluenzavirus, canine distemper virus and canine coronavirus
Canine parainfluenzavirus, canine distemper virus and adenovirus type 1
Canine parvovirus type 2, canine coronavirus and adenovirus type 1
Canine herpesvirus, canine coronavirus and adenovirus type 1
Canine parainfluenza virus, canine coronavirus and adenovirus type 1
Canine distemper virus, canine coronavirus and adenovirus type.

Any of the combinations above can also include antibodies against one, two or three of the following, in any combination:
Bordetella bronchiseptica
E. coli
Streptococci
Staphylococci Any combination of the above can also include antibodies against one or both of the following:
Isospora
Giardia Product example (a): antibodies against canine parvovirus type 2 and against E. coli for early supplementation (before 24 hours of life, systemic)

Product example (b): antibodies against canine coronavirus and against canine parvovirus type 2 (local)

Product example (c): antibodies against distemper virus and against adenovirus type 1.

Product example (d): antibodies against canine herpes virus (an early supplementation) (before 24 hours of life).

Example concerning early supplementation (first day of life):

Half of the specific IgY (representing an unknown part of the total IgY content) can contain specific antibodies against canine parvovirus type 2) and half of it can contain specific antibodies against E. coli).

Example concerning late supplementation (after or separate from the early supplementation):

Half of the specific IgY (representing an unknown part of the total IgY content) can contain specific antibodies against canine parvovirus type 2) and half of it can contain specific antibodies against canine coronavirus).

The composition according to the first aspect of the invention can act to improve dog health as by improving digestive immunity and/or increasing growth and/or reducing stress.

The effect of the composition being administered accordingly is to improve dog health and zootechnical performances by improving general and digestive immunity.

The effect of early administration (within the first 24 hours of life) of specific antibodies is to increase the systemic immunity. The specific antibodies will be absorbed to the blood flow, giving an immediate long-lasting protection after a single (and then possibly double) dose. Thus, the invention has two routes of positive actions according to the time of administration. Early administration (before 24 hours) permits specific antibodies to pass through the intestine barrier to reach the blood system. This results in systemic protective action which may be against at least the pathogens targeted by the vaccination program applied to the animal producing the hyperimmunised solution by its own vaccination response). The composition of the first aspect of the invention is able to act before the intestinal barrier closes if given before 24 hours of age as antibodies of the hyperimmunised solutions go directly into the blood flow. Given at or after 24 hours of age, the composition modulates and positively regulates the consequences of stress in the animal (such as weaning, transportation, intensive exercise, etc) in the digestive tract, including parasitic load, inflammation, microflora equilibrium disturbance etc. When given at or after 24 hours of age, the effect is a local effect in the digestive liner/oral cavity.

The composition of the invention may be administered once or twice before 24 hours. The composition may be administered before 8 hours of life, including twice before 8 hours of life, at least 4 hours apart. This administration may maximize the antibodies entering the systemic circulation of the animal. Administration at 24 hours of age and afterwards may be at least once a day or more often. The same or a different composition according to the invention may be administered before 24 hours of age and at 24 hours of age and afterwards.

After the first day of life, the recommendation will be the same as those for dog milk products, as described below:

| | Dog size as adult/Amount | | | | |
|---|---|---|---|---|---|
| Age (weeks) | Dosage/ per 24 hours | Mini 1-10 kg 0-20 lb | Medium 11-25 kg 2155 lb | Maxi 26-44 kg 56-100 lb | Giant >45 kg >100 lb |
| 1 | ×8 | 3-10 ml | 5-20 ml | 10-25 ml | 15-35 ml |
| 2 | ×5 | 10-30 ml | 15-50 ml | 37-70 ml | 40-80 ml |
| 3 | ×4 | 20-50 ml | 35-90 ml | 60-120 ml | 85-125 ml |
| 4 | ×4 | 25-60 ml | 45-125 ml | 90-170 ml | 120-190 ml |

| Age weeks | Dosage/per 24 hours | Amount |
|---|---|---|
| 1 | ×7 | 2-4 ml |
| 2 | ×6 | 5-10 ml |
| 3 | ×5 | 10-15 ml |
| 4 | ×5 | 10-15 ml |

The product can be formulated as follows:

Proportion of egg powder according to 4 scenarios related to a product suitable to be sprayed:

Scenario 1: the use of whole egg powder diluted in oil and/or fat without dextrose:

Proportion of hyperimmunised whole egg powder from 5 to 30% of the product (based on a supplement used in a spray).

Scenario 2: the use of whole egg powder diluted in oil and/or fat with dextrose:

Proportion of hyperimmunised whole egg powder from 5% to 30% of the product with dextrose from 10% to 30% (based on a supplement used in a spray).

Scenario 3: the use of yolk egg powder diluted in oil and/or fat without dextrose:

Proportion of hyperimmunised whole egg powder from 1% to 20% of the product (based on a supplement used in a spray).

Scenario 4: the use of yolk egg powder diluted in oil and/or fat with dextrose:

Proportion of hyperimmunised whole egg powder from 1% to 20% of the product with dextrose from 10% to 30% (based on a supplement used in a spray).

A second aspect of the invention provides a composition according to the first aspect of the invention, without limitation as to the use or administration regime.

Accordingly, a second aspect of the invention provides a composition containing antibodies against one or more of the following:

Virus:
  Canine parvovirus type 2,
  Canine Herpesvirus,
  Canine parainfluenza virus
  Canine distemper virus
  Canine coronavirus
  Adenovirus type 1
Bacteria:
  *Bordetella bronchiseptica*
  *E. coli*
  Streptococci
  Staphylococci
Parasite:
  *Isospora*
  *Giardia*

All preferred features of the first aspect also apply to the second. This includes that the composition may comprise hydrolysed carbohydrate and/or oil (or fat) as set out according to the first aspect of the invention, including the amounts given.

The oils may be as described above for the first aspect of the invention. Additional other ingredients may also be described above according to the first aspect of the invention. The antibodies can be produced according to the above described methods. The format of the second aspect of the invention is as described above in relation to the first aspect.

For improving dog health, preferably where the dog is in need of health improvement, comprising administering a composition containing antibodies against one or more of the following:

Virus:
  Canine parvovirus type 2,
  Canine Herpesvirus,
  Canine parainfluenza virus
  Canine distemper virus
  Canine coronavirus
  Adenovirus type 1
Bacteria:
  *Bordetella bronchiseptica*
  *E. coli*
  Streptococci
  Staphylococci
Parasite:
  *Isospora*
  *Giardia*

Preferably, the administration of the composition is before 24 hours of age or 24 hours onwards.

More preferred features of the first and second aspect of the invention, also apply to the third aspect.

In particular, the third aspect of the invention relates to a composition according to the first and/or second aspect of the invention. The administration may be from 24 hours onward up to 70 days of age or up to 90 days of age.

The invention relates to improving dog health, in particular the health of puppies from birth to weaning (around 2 months of age). Improvements in health may be evidenced by improvements in digestive immunity, growth and/or stress.

In addition, the health to be improved relates to infectious diseases (including septicaemia and diarrhoea), parasites, inflammation and microflora equilibrium disturbance (which relates to gut health). In particular, the composition relates to the prevention and/or treatment of infections relating to the particular virus, bacteria or parasites to which the antibodies present in the composition are raised.

The present invention is described with reference to the following non-limiting examples:

EXAMPLES

Example 1

Introduction:

Immunoglobulin therapy has been used for decades in human and veterinary medicine to treat or prevent infectious diseases in preterm neonates or those with passive immune failure. Undeniably, correct weight gain (WG) reflects a good health status. The aim of this study was to evaluate the effect of immunoglobulins administration on weight gain in puppies.

Materials and Methods:

The protocol is conducted in a commercial kennel with various breeds (300 bitches).

Protocol:
Two schemes of supplementation are evaluated:
Early supplementation: four and eight hours after birth, puppies receive an oral supplementation with immunoglobulins
Late supplementation: puppies receive an oral supplementation every 3 days from Day 2 until Day 60.

Puppies are fed by maternal colostrum/milk and are then progressively weaned. At birth, they are allocated in one of the four following groups:
No supplementation (00)
Early supplementation only (E0)
Early and Late supplementation (EL)
Late supplementation only (0L)

The work is conducted as follows:
Proof of concept: supplementation is provided through canine immune serum.
Impact of the Immunoglobulins Supplementation on General Immunity, Digestive Health and Mortality Rates: Supplementation with Canine Serum
Canine Serum Collection Adult dogs are vaccinated against Distemper, Adenovirus, Parvovirus, Parainfluenza, *Bordetella* (one injection) and against Herpesvirus 1 (two injections, two weeks apart). Two weeks after the second vaccination, blood is collected by catherization of the jugular vein after surgical preparation of the area.

Blood collection (for serum preparation) is be performed on:
adult dogs with a body weight higher than 10 kg
for males, no restriction other than body weight is applied;
for females, those within the last month of anoestrus, those pregnant or within the first month of lactation are excluded.

Each animal is weighed before blood collection. The quantity of blood collected is calculated as 7 mL/kg body weight. For non-repetitive blood sampling, Hohenhaus, (2006) and Frey (2009) found non deleterious collection rate of 17 mL/kg, Schneider (1995) collecting 22 mL blood/kg body weight.

Serum is extracted by clotting at room temperature and centrifugation. It is aliquoted in 4 mL tubes under sterile atmosphere (laminar hood). A bacteriological analysis (anaerobe and aerobe culture) is conducted before administration.

Figure 3:
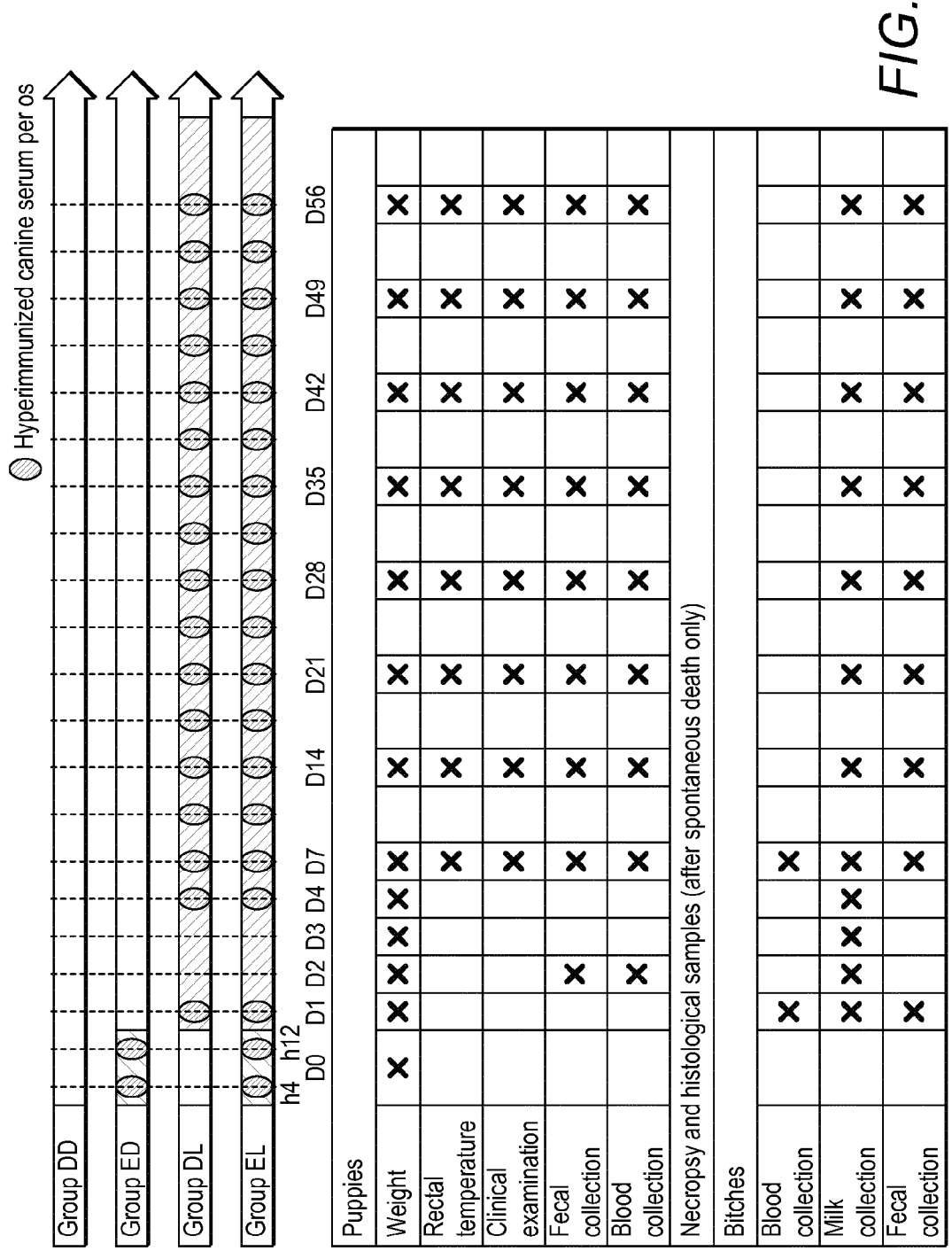

Management of Puppies (FIG. 3)

240 OR 320 puppies are included. Allocation within a group is randomised taking into account the weight at birth (division in quartiles in proportion of the adult weight). Puppies are identified thanks to a coloured wool collar. This technique has already proven to be safe in the same kennel for the puppies and their mother (no strangulation, no ingestion, no limb striction). The collar is renewed every week at the time of manipulation for sampling, in order to follow the puppies growth.

From Day 1 to Day 4: weight
From Day 7 to Day 63 once a week:
weight, clinical examination, rectal temperature measurement (smooth appropriate tip)
administration of 15 mL serum/kg puppy per os (feeding tube during the first week and feeding syringe after)
faeces collection Method: Faeces are collected after spontaneous defecation and by intrarectal cotton swabbing (one swab for virus load; one for microbiota) for:
faecal scoring (from Day 28) based on Royal Canin scale adapted for puppies by Grellet
faecal microbiota
quantification of the viral charge (parvovirus/coronavirus)
quantification of the parasitological charge (*Isospora, Toxocara, Giardia*)
digestive health markers assay (calprotrectin)
digestive immunity markers (total immunoglobulins A; antiparvovirus and anticoronavirus antibodies)
blood collection Method: Blood is collected from the jugular vein in puppies maintained in lateral or dorsal recumbency. The vein is evidenced with some sterile water being poured locally. Collection is performed thanks to a 23 G needle and a 2 mL syringe. Digital compression of the puncture site is then ensured for 1 minute. The puppy is released only after checking of the absence of any persistent bleeding. A maximum of 0.7 mL of blood per 100 g body weight puppy is collected. The collection of 10% of the circulating volume is possible without any disturbance, with circulating volume representing 8% body weight: the maximal volume is thus 0.8 mL per 100 g puppy. Such a protocol has already been used successfully in 56 puppies sampled at Day 0, Day 2, Day 7 and once a week until Day 60 without any mortality induced by blood collection (Chastant-Maillard et al, 2010) and in 20 puppies collected once a week from Day 0 to Day 56 (Casseleux, 2007).
for
total immunoglobulins assay
specific antibodies assay (parvovirus, herpesvirus, coronavirus)
citrullin Serum originating from hyperimmunized dogs has been prepared and stored in −20° C. before the experiment onset. Breed size, weight and health status of each newborn puppy were recorded since birth till d56 every week. Depending on type and time of serum administration puppies were assigned to 4 different groups early (EO, n=36), early and late (EL, n=34), late (OL, n=41) and control (OO, n=38). Puppies from EO and EL received serum orally (1.5 ml/100 g b.w.) 2 times within the first 8 hours of life. Puppies from EL and OL received serum orally (3 ml/puppy) 2 times per week since D2 til D52. Data were analysed with Chi square (morbidity) and ANCOVA (weight gain) tests.

Results

Figure 2:
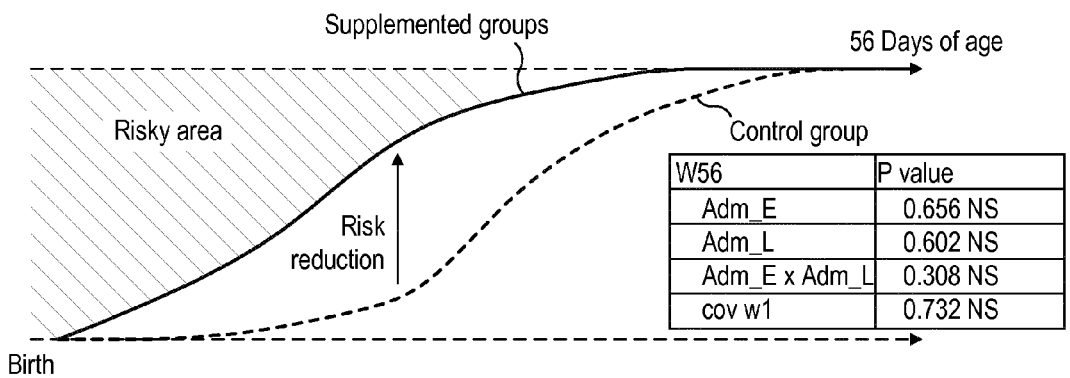

During the first 21 days of life puppies from groups early supplemented (EO and EL) presented significantly less clinical signs of diseases than puppies from other groups (OL and OO) (16% (11/70) vs. 30% (24/79), p=0.045). Within D2-28 there was a tendency to greater WG in large breed puppies early supplemented (EO, EL mean 786.6 g vs. OL, OO 717.9 g; p=0.078) and in small breed puppies late supplemented (EL, OL 730.4 g vs. EO, OO 731.8 g). The results are shown in FIG. 1 and FIG. 2. Within D29-49 WG was significantly greater in large breed puppies late supplemented comparing with other puppies (EL, OL 2445.7 g vs. EO, OO 2294.0 g; p=0.006).

CONCLUSIONS

In this study, puppies supplemented with adult serum before gut closure manifested any pathology within the neonatal period less often. Better WG was observed in early and late supplemented animals until weaning. It shows that immunoglobulin therapy is a prophylaxis against morbidity and for health in puppies.

Results are shown in FIGS. 1 and 2.

FIG. 1 shows first results on morbidity. Significant results from start—Step 1—Morbidity=visible signs of a disease on an alive puppy in a period. Early supplementation significantly REDUCED MORBIDITY.

FIG. 2 shows first results on growth. Significant results from start—LARGE DOG growth rate improved. A control group in a breeding kennel is NOT a safe group (virus and parasite infections). Before 2 months of age the fastest growth is the safest for the puppy.

FIG. 3 shows the sampling protocol.

The invention claimed is:

1. A method of improving dog health, the method comprising orally administering to a dog a composition containing antibodies against Canine parvovirus type 2 in combination with antibodies against one of the following;
Canine coronavirus,
*E. coli,*
Canine Herpesvirus,
optionally, also in combination with antibodies against one or more of the following:
*Bordetella bronchiseptica*
*Giardial*
Canine parainfluenza virus,
Canine distemper virus,
Adenovirus type 1,
Streptococci,
Staphylococci or
*Isospora;*
wherein the oral administration occurs at least once during the first 24 hours of the dog's life and at least every three days between 48 hours of age and 60 days of age and wherein the antibodies are produced by a mammal.

2. The method of claim 1, wherein the composition also comprises a hydrolysable carbohydrate and/or oil.

3. The method of claim 1, wherein the oral administration occurs at least twice during the first 24 hours of the dog's life.

4. The method of claim 1, wherein the improvement in the dog's health is an improvement in the dog's digestive immunity.

5. The method of claim 1, wherein the improvement in the dog's health is an increase in the dog's growth.

6. The method of claim 1, wherein the improvement in the dog's health is a reduction in the dog's stress.

7. The method of claim 4, wherein the administration results in an increase in the systemic immunity of the dog.

8. A method for preventing disease or enhancing weight gain in a dog, comprising orally administering to a puppy at least once before 24 hours of age and at least every three days between 48 hours of age and 60 days of age a composition comprising antibodies against canine parvovirus type 2 in combination with antibodies against at least one of canine coronavirus, *E. coli,* canine herpesvirus, *Bordetella bronchiseptica,* Giardial, canine parainfluenza virus, canine distemper virus, adenovirus type 1, Streptococci, Staphylococci and/or *Isospora,* wherein the antibodies are produced by a mammal.

* * * * *